United States Patent [19]
Vaghefi

[11] Patent Number: 5,875,776
[45] Date of Patent: Mar. 2, 1999

[54] DRY POWDER INHALER

[75] Inventor: Farid Vaghefi, Culver City, Calif.

[73] Assignee: Vivorx Pharmaceuticals, Inc., Santa Monica, Calif.

[21] Appl. No.: 629,605

[22] Filed: Apr. 9, 1996

[51] Int. Cl.$^6$ ............................................. A61M 15/00
[52] U.S. Cl. .................................. 128/203.15; 128/203.12; 128/203.21
[58] Field of Search ...................... 128/203.12, 203.15, 128/203.21, 205.21; 604/58

[56] References Cited

U.S. PATENT DOCUMENTS

| | | | |
|---|---|---|---|
| 1,642,950 | 9/1927 | Haas | 604/58 |
| 2,147,158 | 2/1939 | Goldenthal | 604/58 |
| 3,425,414 | 2/1969 | Le Roche | 128/203.21 |
| 3,739,950 | 6/1973 | Gorman | 128/200.23 |
| 3,856,142 | 12/1974 | Vessalo | 128/200.23 |
| 4,509,515 | 4/1985 | Altounyan et al. | 128/203.15 |
| 4,796,614 | 1/1989 | Nowacki et al. | 128/200.23 |
| 4,957,656 | 9/1990 | Cerny et al. | 252/311 |
| 5,239,991 | 8/1993 | Chawla et al. | 128/203.15 |
| 5,267,555 | 12/1993 | Pajalich | 128/202.25 |
| 5,287,850 | 2/1994 | Haber et al. | 128/203.21 |
| 5,327,883 | 7/1994 | Williams et al. | 128/203.12 |
| 5,349,947 | 9/1994 | Newhouse et al. | 128/203.21 |
| 5,354,562 | 10/1994 | Platz et al. | 424/489 |
| 5,354,934 | 10/1994 | Pitt et al. | 514/8 |
| 5,364,838 | 11/1994 | Rubsamen | 514/3 |
| 5,383,850 | 1/1995 | Schwab et al. | 604/58 |
| 5,388,572 | 2/1995 | Mulhauser et al. | 128/203.15 |
| 5,388,573 | 2/1995 | Mulhauser et al. | 128/203.15 |
| 5,392,768 | 2/1995 | Johansson et al. | 128/200.14 |
| 5,394,866 | 3/1995 | Ritson et al. | 128/200.14 |
| 5,394,868 | 3/1995 | Ambrosio et al. | 128/203.15 |
| 5,415,162 | 5/1995 | Casper et al. | 128/203.12 |
| 5,634,900 | 6/1997 | Makino et al. | 604/58 |

FOREIGN PATENT DOCUMENTS

| | | |
|---|---|---|
| 0 634 184 A1 | 1/1995 | European Pat. Off. . |
| WO 91/16038 | 10/1991 | WIPO . |
| WO 93/00951 | 1/1993 | WIPO . |
| WO 94/08552 | 4/1994 | WIPO . |
| WO 94/23772 | 10/1994 | WIPO . |
| WO 95/07724 | 3/1995 | WIPO . |
| WO 95/11666 | 5/1995 | WIPO . |
| WO 95/11715 | 5/1995 | WIPO . |

OTHER PUBLICATIONS

Barnes, Peter J., "Inhaled Glucocorticoids For Asthma." *The New England Journal of Medincine* 322 (13): 868–875 (1995).

Bell et al., "Dry Powder Aerosols I: A New Powder Inhalation Device." *Journal of Pharmaceutical Sciences* 60 (10) : 1559–1564 (1971).

Cicerone et al., "Stratosphric Ozone Destruction by Man--Made Clorofluoromethanes." *Science* 185: 1165–1167 (1974).

Clay et al., "Assessment Of Jet Nebulisers For Lung Aerosol Therapy." *The Lancet*:592–594 (1983).

Clay et al., "Factors influencing the size distribution of aerosols from jet nebulisers." *Thorax* 38: 755–759 (1983).

Cockcroft et al., "Importance of Evaporative Water Losses During Standardized Nebulized Inhalation Provocation Tests." *Chest* 96(3) : 505–508 (1989).

Hallworth, G. W., "The formulation and evaluation of pressurised metered–dose inhalers." In *Drug Delivery to the Respiratory Tract* (Garderton and Jones, eds.) Ellis Horwood, Engl., pp. 87–118 (1987).

Jones, Kevin, "New delivery system for asthma drugs." *The Practitioner* 233: 265–267 (1989).

Kelsen et al., "Airborne Contamination of Fine–Particle Nebulizers." JAMA 237 (21) : 2311–2314 (1977).

Kongerud et al., "Room temperature influences output from the Wright jet nebulizer." *Eur. Respir.* J. 2: 681–684 (1989).

Newman, Stephen P., "Therapeutic aerosols." In *Aerosols and the Lung:Clinical and Experimental Aspects.* (Clarke and Pavia, eds.) Butterworths, Chapter 9. (1987).

Popa et al., "Domiciliary metaproterenol nebulization: A bacteriologic survey." *J. Allergy Clin. Immunol* 82 (2) : 231–236 (1988).

Ribeiro and Wiren, "Comparison of Bricanyl Turbuhaler and Berotec dry powder inhaler." *Allergy* 45: 382–385 (1990).

Sterk et al., "Physical Properties Of Aerosols Produced By Several Jet–And Ultrasonic Nebulizers." *Bull. Eur. Physiopathol. Respir.* 20: 65–72 a91984).

Tillery et al., "Generation and Characterization of Aerosols and Vapors for Inhalation Experiments." *Environmental Health Perspectives* 16: 25–40 (1976).

Witek and Schachter, Detection of Sulfur Dioxide in Bronchodilator Aerosols. *Chest* 86(4) : 592–594 (1984).

Wetterlin, Kjell, "Turbuhaler: A New Powder Inhaler for Administration of Drugs to the Airways." *Pharmaceutical Research* 5 (8) : 506–508 (1988).

*Primary Examiner*—Aaron J. Lewis
*Attorney, Agent, or Firm*—Gray Cary Ware & Freidenrich, LLP; Stephen E. Reiter

[57] ABSTRACT

A dry powder inhaler includes a housing, a dosing cartridge, and a spacer. Within the housing are a source of pressurized gas, a pressure gauge, a metered valve controlled by a trigger, a safety valve, and an electrostatic charger also controlled by the trigger. The dosing cartridge contains individual doses in airtight cells with one or more openings, each covered by an airtight coversheet. The system uses gas pressure or a penetration device to rupture one of the airtight cells, suspending the powder and directing it to a spacer for subsequent inhalation. The electrostatic charger discharges on the spacer, establishing an electrostatic charge thereon. The spacer includes a non-stick lining. The housing is designed so that it can retract into the spacer.

27 Claims, 5 Drawing Sheets

FIG. 8

FIG. 9

DRY POWDER INHALER

FIELD OF THE INVENTION

This invention relates to technology for dispensing dry powder pharmaceuticals and, more particularly, to dry powder inhalers and dosing cartridges for administration of pharmaceuticals to the lung, and to methods for dispensing dry powder pharmaceuticals by inhalation.

BACKGROUND OF THE INVENTION

Among the varied forms of pharmaceutical delivery, the inhalation of dry powder is preferable for some forms of pharmaceuticals. Inhalation does not require passing the pharmaceutical through the digestive system (as required by ingestion), and avoids the sometimes difficult and distasteful alternative of patients injecting themselves. For example, inhalation is often preferred for pharmaceuticals used to treat respiratory diseases.

During inhalation, a user receives a dose of a pharmaceutical in an inhaled airstream. The pharmaceutical optimally travels into the lungs where it is absorbed. Efficient delivery of powdered pharmaceuticals is dependent on the dispensing technique and particle size of the powder. Optimally, the particles should be 5 microns or less in size.

The use of a dry powder pharmaceutical for inhalation offers numerous advantages over aqueous or aerosol pharmaceuticals. Nebulizers, used for delivery of aqueous pharmaceuticals, are generally large and cumbersome devices that are complex to operate. The dosage precision provided by a nebulizer may vary depending on a variety of factors, e.g., atmospheric temperature and humidity, and the volume and strength of the patient's breathing. Furthermore, aqueous solutions do not generally provide an inert vehicle for the pharmaceutical, and thus drug stability is also an issue.

Metered Dose Inhalers (MDIs), used for delivering aerosolized pharmaceuticals, frequently work with chlorofluorocarbon propellants, which are in disfavor due to environmental concerns. Other media have not yet proven commercially viable. Furthermore, MDIs are sensitive to particle size, and frequently require additional dispersing agents to achieve proper drug dispersal. MDIs generally spray the particles into the mouth, and thus the administered dose frequently suffers from the particles, particularly larger ones, striking the back of the throat and not reaching the lungs. This problem is accentuated by the need for the patient to coordinate actuation and breathing.

While it offers advantages over other types of pharmaceutical delivery, the technology for inhaling dry powder presently suffers an array of difficulties limiting its usefulness to patients. Prior to delivery, powdered pharmaceuticals may deteriorate or form excessively dense agglomerations due to exposure to moisture. Some measures to protect the pharmaceutical, such as storage in capsules that must be broken to release the powder, require cumbersome procedures in preparing the inhaler for use. Even when kept dry, the powdered pharmaceuticals may tend to form an agglomerate that must be broken into finer particles for delivery.

There are also numerous problems related to the actual delivery of dry powder pharmaceuticals. Many devices rely on inhalation by the patient to provide the power to break up the dry material into free-flowing powder. These devices prove ineffective for those lacking the capacity to strongly inhale, such as young patients, old patients, or patients with asthma. Other devices spray the pharmaceutical into the mouth, requiring breathing to be coordinated with the spray. During delivery, large quantities of particles may become deposited on the delivery mechanism, reducing the "uptake efficiency" of the device. On passage into the mouth, the walls of the mouth and/or throat may absorb particles, causing a further loss in uptake efficiency. This problem is particularly dramatic when the pharmaceutical is sprayed into the mouth, rather than being gently inhaled. Numerous dry powder inhalers use gravity-sensitive reservoirs of dry powder, requiring the inhaler to be held at a proper angle relative to gravity for the powder to be effectively delivered. Additionally, many delivery mechanisms are large and/or expensive, problems which may be magnified when a patient requires several types of medication, each requiring the cost and inconvenience of a separate inhaler.

One apparatus for producing an aerosolized dose of a pharmaceutical for subsequent inhalation by a patient is disclosed in PCT International Publication No. WO93/00951 (published Jan. 21, 1993), by Inhale, Inc., incorporated herein by reference. The disclosed apparatus includes a trigger, controlling the release of gas from a gas cylinder, where the gas passes through a venturi that draws the dry powder from a reservoir. The gas passes to a chamber with a mouthpiece, from where a patient may breathe in the pharmaceutical. The chamber may be cylindrical, and include a one-way air inlet. The apparatus may be small enough to be hand-held.

The apparatus shown in the Inhale, Inc. application provides for storage and provision of a pharmaceutical from a reservoir, drawing the pharmaceutical out of the reservoir into a flowing air stream. As in any filled reservoir system, the powder may be exposed to contaminants or humidity prior to delivery. Thus, there is a risk of decomposition and excessive agglomeration. Even when dry, the powder might agglomerate, stick to the delivery mechanism or chamber, or not be fully delivered because the gravity-sensitive reservoir is not in a fully upright orientation. In use, the inhaler requires pumping a lever several times to bring the unit up to pressure. This can prove difficult when a patient is suffering from the onset of breathing difficulties. Furthermore, the inhaler cannot be interchangeably used with more than one type of pharmaceutical, and thus the inconvenience and cost are magnified if a patient requires multiple types of pharmaceuticals.

PCT International Publication No. WO94/08552 (published Apr. 28, 1994), by Dura Pharmaceuticals, Inc., shows an inhaler with a pharmaceutical stored in a multi-dosage medicine containing cartridge held between two plates. A plunger is used to thrust powder out of the cartridge and into a stream of air agitated by a motorized impeller. As with the Inhale, Inc. application described above, this device is plagued with the orientation limitations of a gravity-sensitive reservoir-based inhaler. Exposure to contaminants and moisture may cause decomposition of the pharmaceutical. The use of the plunger may compress the pharmaceutical into a more tightly packed agglomerate. Pulverization of this agglomerate is still limited by the patient's ability to inhale. Furthermore, the inhaler may not be used with multiple medications without risk of further exposing the pharmaceutical to decomposition. Finally, the pharmaceutical might deposit on the complex plunging and agitating mechanisms, limiting the uptake efficiency of the device.

U.S. Pat. No. 5,349,947 to Newhouse et al., discloses an inhaler with individual doses of a pharmaceutical stored in blisters. A blister is crushed between a piston and a cylinder, explosively releasing the air and pharmaceutical contained therein. The air and pharmaceutical are propelled into a chamber from which they may be inhaled. The device taught by Newhouse can leave substantial deposits of powder in the blister and/or chamber, reducing the uptake efficiency of the device.

U.S. Pat. No. 5,388,572 to Mulhouser et al., discloses a dry powder inhaler having a pharmaceutical impregnated in a mesh disk. Inhalation triggers the delivery of pharmaceutical, the suction activating a burst of manually pumped up air through the mesh disk. This inhaler potentially allows contamination of the pharmaceutical (from exposure to moisture and contaminants), lowers the uptake efficiency (by shooting powder into the mouth at high speed), and does not provide easy switching of pharmaceutical containers for multiple types of pharmaceuticals.

Accordingly, there exists a definite need for a dry powder pharmaceutical delivery device that can interchangeably provide different powdered pharmaceuticals, which have been safely stored to maintain stability until dispensing, without excessive loss of uptake efficiency due to deposition within the mechanism or to excessive absorption within the mouth or throat. There is a further need for such a device to be conveniently portable without being overly expensive. The present invention satisfies these and other needs, and provides further related advantages.

BRIEF DESCRIPTION OF THE INVENTION

The present invention provides a dry powder inhaler and dosing cartridge, and a method for dispensing a dose of a dry powder pharmaceutical for inhalation. Through a novel combination of features, the invention provides for stable pharmaceutical storage prior to inhalation, and increased uptake efficiency during use. The invention inhaler alleviates problems encountered by prior art inhalers, e.g. problems related to aerosol generation, deposition of pharmaceuticals within the inhaler, absorption of pharmaceuticals within the patient's mouth or throat, and the like. Thus, the invention inhaler maximizes the effective amount of deliverable pharmaceutical. The invention inhaler further provides these benefits in a conveniently portable package that may readily be interchangeably used for several different pharmaceuticals.

In accordance with a particular embodiment of the present invention, there is provided a dry powder inhaler, and method for the use of the above-described inhaler to dispense a dry powder pharmaceutical for inhalation. The dry powder inhaler of the invention includes a source of pressurized gas, the release of which is controlled by a first valve. The source of pressurized gas is connected to a pressure-driven pharmaceutical delivery system. In this system, a dose of pharmaceutical is stored in an airtight cell within a cartridge, and is extracted therefrom by a blast of pressurized gas. After extraction, the pharmaceutical and gas are routed into a spacing device that includes a mouthpiece, and may include a non-stick inner surface. An electrostatic charger is discharged within the spacing device, providing a charge on the inner surface of the spacing device to prevent powder deposition thereon. A patient may then inhale the pharmaceutical. After the dose of pharmaceutical is inhaled, the cartridge may be repositioned to access another cell within the cartridge.

The airtight cell of the invention dosing cartridge provides clean and dry storage for the pharmaceutical, preventing early decomposition or excessive agglomeration of the pharmaceutical. Upon actuation of the inhaler, the explosive blast of gas effectively suspends the pharmaceutical in the gas, breaking up any agglomerates that do form and preventing deposition of pharmaceutical in the inhaler. Good uptake efficiency is thus provided without requiring strong inhalation by the patient. Upon routing to the spacer, the blast of gas is contained for subsequent inhalation so as to avoid uptake loss from deposition on the mouth or throat of the patient. Such deposition could otherwise have occurred if the blast entered the mouth directly, particularly if inhalation did not occur precisely when the blast entered the mouth.

BRIEF DESCRIPTION OF THE DRAWINGS

FIG. 1 is a schematic representation of a dry powder inhaler and dosing cartridge embodying features of the present invention.

FIG. 2 is a plan view of a dry powder inhaler and dosing cartridge embodying features of the present invention.

FIG. 3 is a perspective view of the dry powder inhaler depicted in FIG. 2, wherein the inhaler includes a housing that has been retracted into a spacer.

FIG. 4 is a cut-away view of a portion of the dry powder inhaler shown in FIG. 2. The cut-away view details an air cylinder and a mechanism for installing the air cylinder, taken along line 4—4 of FIG. 2.

FIG. 5 is an end view of the dosing cartridge depicted in FIG. 2.

FIG. 6 is a cross-sectional view of the dosing cartridge depicted in FIG. 5, taken along line 6—6 of FIG. 5, with the addition of coversheets and septa.

FIG. 7 is a cross-sectional view of the dosing cartridge depicted in FIG. 5, with the addition of two coversheets, as aligned with an entrance port and an exit port.

FIG. 8 is a cross-sectional view of a piercing needle mechanism useful in an alternate embodiment of a dry powder inhaler and dosing cartridge embodying features of the present invention.

FIG. 9 is the cross-sectional view of FIG. 8, wherein a suspension system has ruptured an entrance and exit on a cell within the dosing cartridge.

DETAILED DESCRIPTION OF THE INVENTION

An embodiment of a dry powder inhaler according to the present invention is schematically diagramed in FIG. 1. In accordance with the present invention, there is supplied dry powder inhaler 10 providing for repeated inhalation of pharmaceuticals suspended in a gas. The inhaler is for use with removable dosing cartridge 12 that includes a dry powder pharmaceutical sealed within a cell 14, the cell having one or more sealed openings 16 and 18. For some embodiments, each cell must have two or more sealed openings. The dosing cartridge 12 comprises a cartridge body defining cell 14 for containing a dry powder pharmaceutical. The cartridge body further defines the sealed openings. The dosing cartridge further comprises one or more rupturable coversheets 20 and 22 forming an airtight seal over each cell opening. There may be a plurality of cells.

Invention inhaler comprises mouthpiece 24 and a housing (not shown) adapted to removably receive the dosing cartridge. The housing contains first valve 26, and defines three passages 28, 30 and 32. The first passage, 28, includes a connection adapted for connecting to a source of pressurized gas, 34. Any gas that may be inhaled, e.g., nitrogen, $CO_2$, air, and the like, may be used. Air is the presently preferred gas.

The first valve 26 controls the flow of gas from first passage 28 to second passage 30. Trigger 36 actuates the first valve to control the flow of gas, the first valve preferably being metered to release a controlled amount of gas. Second passage 30 and third passage 32 have suspension system 38 for separately connecting to and rupturing openings 16 and 18 of cell 14, and suspending the dry powder. The third passage further connects to mouthpiece 24.

Passages 28, 30 and 32 defined by the housing must be made of a strong material, preferably a metal that will not corrode when moistened. First passage 28 serves to form a connection to the source of pressurized gas 34. The source may be any one of numerous types known in the art, such as an air cylinder, tank of pressurized gas, gas pump, or the like. The source of pressurized gas is preferably a connection to a high pressure air cylinder. Second passage 30 connects to the first passage through valve 26 controlling the flow of gas between the first two passages. Valve 26 must also be made of a strong material, preferably a metal that will not corrode when moistened.

The invention provides for a related method of using a pressurized gas to dispense a dose of dry powder for inhalation. The dose is dispensed from an airtight cell 14 with one or more sealed openings 16 and 18. The method involves rupturing one of the sealed openings to blow the pressurized gas into the cell, thereby pressurizing the cell and suspending the dry powder in the gas. The method further involves separately rupturing one of the sealed openings to allow the pressurized suspension in the cell to flow out of the cell, and directing the flow for inhalation.

In accordance with a related aspect of the present invention, there is provided a dry powder inhaler 10 for dispensing a dry powder pharmaceutical suspended in a gas. The inhaler comprises housing with trigger 36, electrostatic charger 40, hollow spacer 42 connected to the housing, and mouthpiece 24 connected to the spacer. The hollow spacer forms a chamber for receiving a dose of suspended pharmaceutical from the housing.

Upon actuation of trigger 36, the housing delivers the suspended dry powder into spacer 42. Electrostatic charger 40 is adapted to discharge within the spacer upon actuation of the trigger. Deposition of pharmaceutical on the interior surface of the spacer is deterred by the electrostatic charge. Deposition may be further deterred through the use of a non-stick coating (e.g., TEFLON™ brand polytetrafluoroethylene) on the spacer chamber. Mouthpiece 24, on the spacer, provides an opening for a patient to inhale the suspended pharmaceutical.

A related aspect of the present invention provides a method of dispensing a dose of dry powder for inhalation. The method involves forming a suspension from the dry powder in the gas. An electrostatic charge is established on the spacer chamber, and the dry powder and gas are positioned within the chamber to dispense the dry powder for inhalation.

For the practice of the present invention, the housing and spacer 42 may each be any convenient shape, as is readily appreciated by those skilled in the art. Preferably, both the housing and the spacer are the same shape, the spacer being slidably mounted on the exterior of the housing to allow the housing to retract into the spacer. Various cylindrical shapes (e.g., a circular cylinder, an oval cylinder, a rectangular cylinder) are well suited for this retraction feature. Preferably, the shape is of an oval cylinder.

The housing is adapted to removably receive dosing cartridge 12 such that one cell 14 is in an "aligned" position with respect to the second and third passages. Second passage 30 provides a connection to sealed opening 16 of the aligned cartridge cell. Third passage 32 serves to connect sealed opening 18 of the aligned cartridge cell to the spacer 42 chamber. The structure connecting the second passage to the cell and the structure connecting the cell to the third passage forms suspension system 38. The suspension system functions to (1) separately rupture the sealed opening(s) of the cell at the connections, and (2) disperse the pharmaceutical in the gas to form the suspension.

The position of dosing cartridge 12 within the housing is adjustable to allow each cell 14 to move into the aligned position. The dosing cartridge may be any of a multitude of configurations (e.g., linear, disk-shaped) depending on the type of adjustment to be used. A linear dosing cartridge, for example, may be used with a sliding adjustment. The linear cartridge slides through a slot in the housing to consecutively place each cell in the aligned position. A disk-shaped dosing cartridge, as another example, may be used with a rotating adjustment. The disk-shaped dosing cartridge rotates in the housing to consecutively place each cell in the aligned position. A disk-shaped cartridge is presently preferred.

Optional additional features which are preferably included as part of inhaler 10 include a device to monitor the pressure 44 in first passage 28, safety valve 46 to prevent the unrestricted discharge of gas on the occurrence of a failure of first valve 26, and one-way air inlet 48, functionally venting spacer 42 to provide for less resistance during inhalation. The pressure monitor and safety valve should each be made of a strong material, preferably a metal that will not corrode when moistened. The one-way air inlet may be located in second passage 30, third passage 32, or on the spacer.

Figures 1, 3:
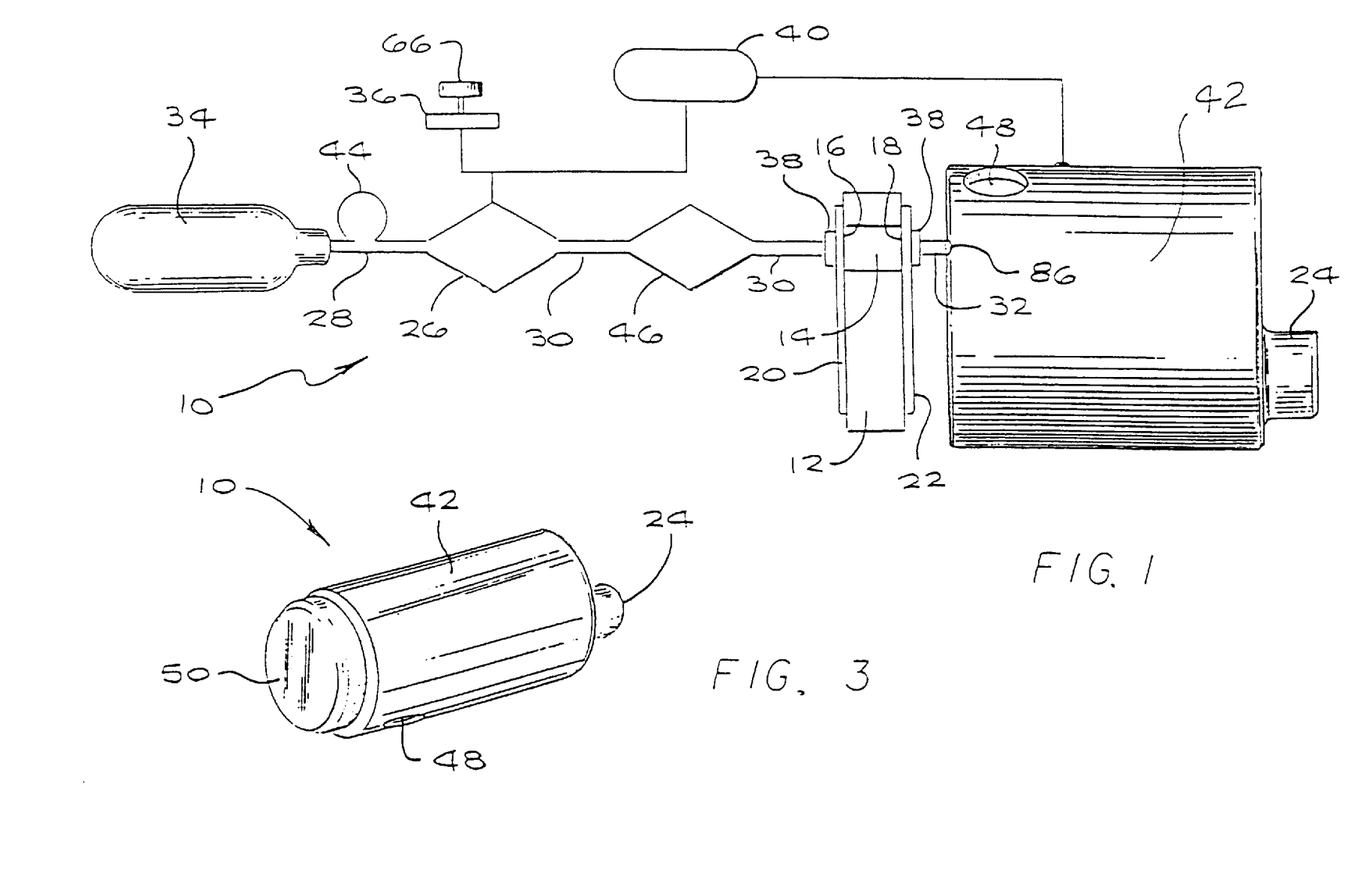
Figures 2, 7:
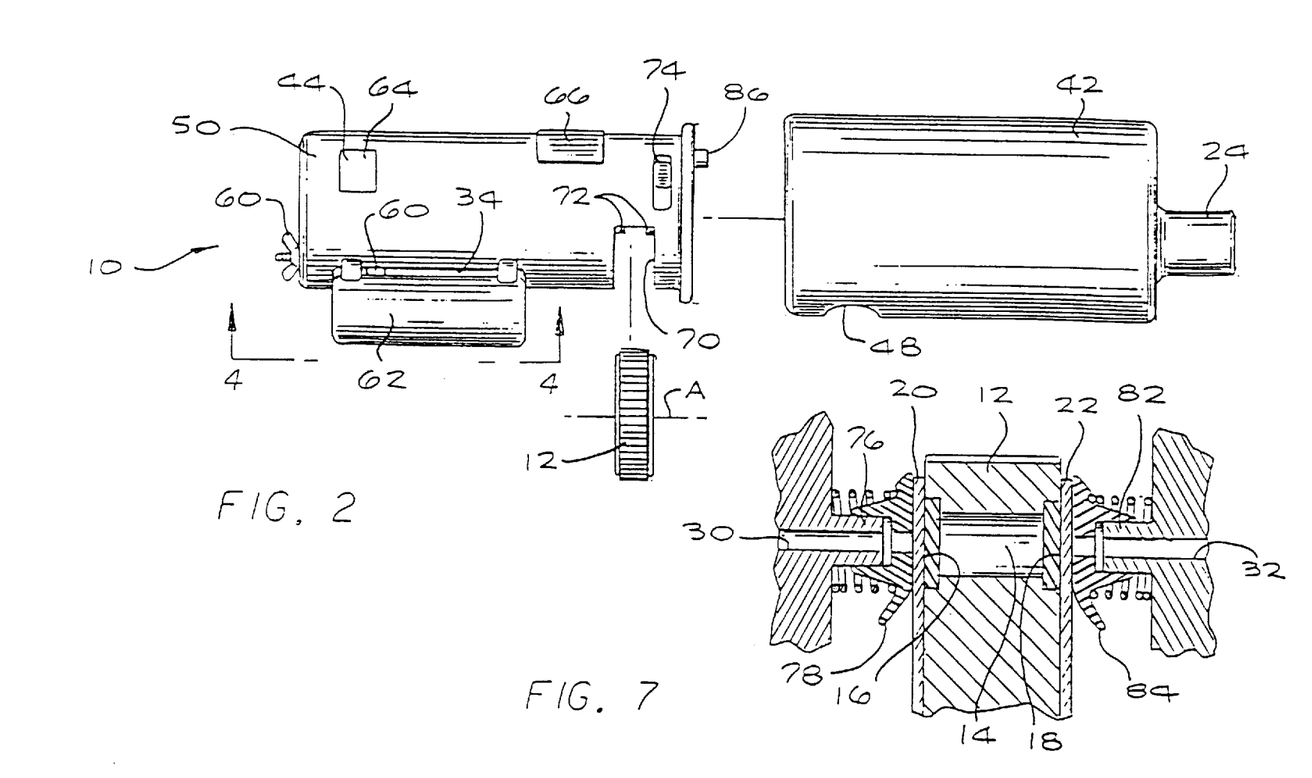

With reference to one preferred embodiment of the present invention (the "blow-through" embodiment), as illustrated in FIGS. 1–3, inhaler 10 has a durable housing 50 and a durable hollow spacer 42 with a mouthpiece 24. Both the housing and the spacer form approximately oval cylinders, the spacer being slidably mounted on the exterior of the housing to allow the housing to retract into the spacer, as depicted in FIG. 3. The spacer preferably is removable from the housing to allow for ease of cleaning. One-way air inlet vent 48 is located on the spacer to provide for less resistance during inhalation.

Air cylinder 34 is conveniently sized to fit in a hand-held package, and is preferably approximately 2.5 inches by 0.75 inches. The air cylinder is pressurized to an adequate level for the unit to function, as described below, which is preferably up to approximately 800 psi.

Figure 4:
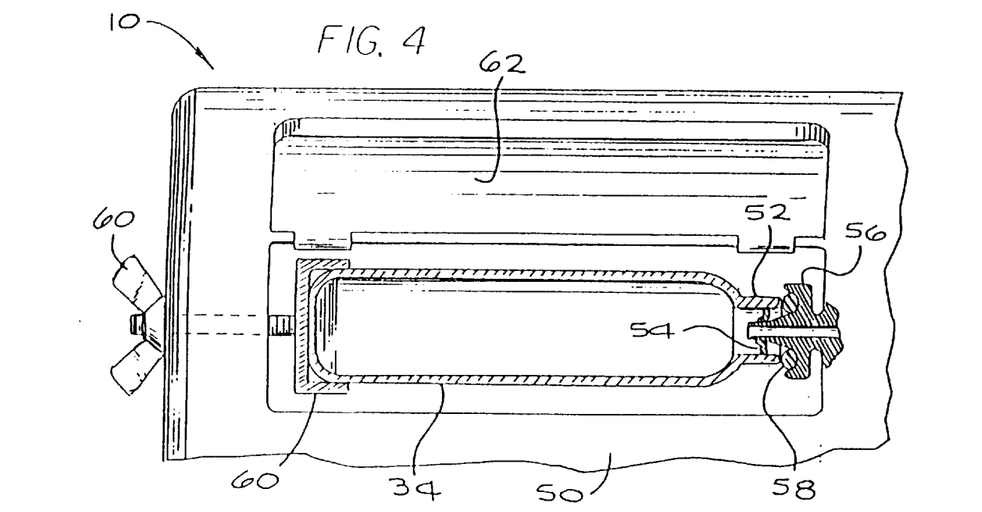

With reference to FIGS. 1, 2 and 4, air cylinder 34 includes a mouth 52 that is sealed by a penetrable cover 54 prior to connection to the inhaler. The connection to a high-pressure air cylinder on housing 50 includes a piercing nozzle 56 conforming with the mouth. Upon installing the air cylinder, the piercing nozzle is received within the mouth, puncturing the penetrable cover. O-ring 58 surrounds the piercing nozzle, forming an air-tight seal between the piercing nozzle and the mouth after the penetrable cover is pierced. For installation, the air cylinder is pressed and held on the piercing nozzle through the use of thumbscrew mechanism 60 which may be operated by the patient when installing the air cylinder.

Piercing nozzle 56 may be mounted on a housing tube (not shown) that forms all or part of air passage 28 into housing 50. The mounting may include O-rings or gaskets, made of a stable sealing material (e.g., silicon rubber), to create an air-tight seal between the piercing nozzle and the tube. Alternately, the piercing nozzle may be integral with the tube. The housing also includes access door 62 for covering the air cylinder when it is received on the piercing nozzle.

With reference to FIGS. 1 and 2, the gas from within installed air cylinder 34 flows into and pressurizes first passage 28. This pressurized passage leads to pressure gauge 44, which is appropriate for use in the pressure ranges provided by the air cylinder. The pressure gauge is located within housing 50 such that its readings are visible through window 64 on the housing.

First passage 28 also leads to metered valve 26. The metered valve, which is generally closed, controls the transfer of pressurized gas into unpressurized second passage 30. Trigger 36 opens metered valve 26, releasing a predetermined amount of gas, preferably being in an amount less than the volume of spacer 42 at normal atmospheric conditions. The gas is released into the second passage, causing a burst of pressurized gas to pass through the second passage.

Trigger 36 includes button 66 protruding through housing 50, allowing actuation of the trigger. The button is positioned so as not to interfere with retraction of the housing within spacer 42. The button preferably includes a return spring that may be varied in stiffness for different preferences of sensitivity.

Second passage 30 continues through safety valve 46. The safety valve rests in an open position, and only impedes the burst of gas if an excessive quantity of gas passes uninterrupted through the safety valve. If the safety valve closes, it remains closed until reset. If the safety valve does not actuate, as is generally the case, the burst of gas passes through and is directed toward opening 16 in dosage carousel 12. It is to be understood that the safety valve may be positioned along first passage 28, second passage 30, or third passage 32. It is, however, preferably positioned along the second passage as shown.

Figures 5, 6:
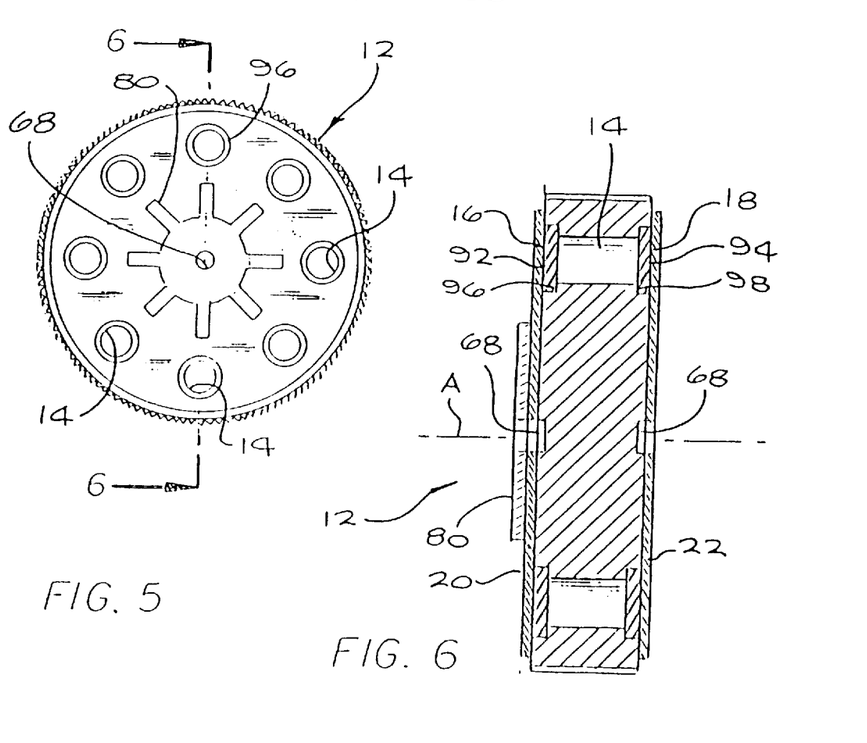

With reference to FIGS. 2, 5 and 6, dosing carousel 12 is illustrated as a disk-shaped body to be mounted within housing 50 such that it may rotate around an axis of rotational symmetry A. The dosing carousel may include two axle sockets 68, each formed from a hole positioned along the axis of symmetry. The housing includes section 70, forming a cavity sized to receive the dosing carousel, including two carousel pins 72, conformed to be received in the axle sockets when the dosing carousel is inserted within the housing. Spring loaded release knob 74 slidably actuates the pins such that the pins retract when the knob is turned, allowing for removal and replacement of the dosing carousel. Alternatively, the pins may be spring loaded to allow removal and insertion of the dosing carousel with the application of adequate force, or the pins may be actuated by opening access door 62. The knob and mounted dosing carousel are both preferably positioned so as not to interfere with retraction of the housing within spacer 42.

With reference to FIGS. 1 and 5–7, dosing carousel 12 is illustrated as defining one or more cells 14, each containing a single dose of a pharmaceutical. The illustrated cells pass through the dosing carousel, each cell having two exterior openings forming entrance 16 and exit 18. Preferably the entrance and exit are aligned with each other in an axial direction as seen in FIG. 6. The entrance and exit are covered by rupturable coversheets 20 and 22. The coversheets are affixed to the dosing carousel body such that each cell is sealed to be airtight. The coversheets protect the pharmaceutical from water and contaminants such as oxidants. As will be apparent to those skilled in the art, the coversheets may be of any of a large variety of materials such as metal foil or plastic. The coversheets are preferably made of aluminum sheet. In an alternative to affixed coversheets, the rupturable coversheets may be integral with the dosing carousel body.

When dosing carousel 12 is properly inserted within housing 50, the entrance 16 to one cell is aligned with entrance port 76 of second passage 30. While the entrance port may be any form of passage ending (e.g., a protrusion or flush hole), it is preferably a cylindrical protrusion. An entrance connector 78 is slidably mounted, preferably on the entrance port, and is spring loaded against entrance coversheet 20. The entrance connector is positioned so as to form a relatively airtight seal between the entrance port and the entrance to the aligned cell. The dosing carousel preferably includes studs 80, each serving as a rotation stop associated with one cell. The housing preferably is provided with a rotation lock mechanism (not shown) that receives each stud in turn to align its associated cell with the entrance port. The locking mechanism may be spring loaded.

With reference to FIGS. 1, 2 and 7, exit 18 of the aligned cell is aligned with exit port 82. While the exit port may be any form of passage ending (e.g., a protrusion or flush hole), it is preferably a cylindrical protrusion at the end of third passage 32. An exit connector 84 is slidably mounted on the exit port, and is spring loaded against exit coversheet 22 so as to form a relatively airtight seal between the exit port and the exit to the aligned cell. The aligned cell thus effectively connects second passage 30 to the third passage. The exit port forms the first end of third passage 32, which also has exhaust end 86 that opens out into spacer 42, effectively connecting the exit port to the spacer chamber, which in turn connects to mouthpiece 24.

Spacer mouthpiece 24 is preferably positioned on spacer 42 at a location distant from exhaust end 86 of third passage 32. One-way air inlet vent 48 is preferably located on the spacer. The hollow spacer chamber includes a non-stick lining. The lining may be any material with a smooth surface such as plastic, but preferably is a material designed to resist sticking. A particularly preferred lining material is TEFLON™ brand polytetrafluoroethylene.

With reference to FIGS. 1, 2, 6 and 7, housing 50 includes electrostatic charger 40, which is also controlled by trigger 36. When fired, the electrostatic charger produces an ionizing charge on the interior of spacer 42 to deter deposition of pharmaceutical on the interior wall thereof.

In practice, the inhaler is generally prepared for use by attaching air cylinder 34 such that first passage 28 is pressurized, as described above, and shutting door 62. Prior to use, spacer 42 is extended, exposing housing 50. If dosing carousel 12 is not already in place, it is inserted such that housing pins 72 are aligned and inserted in axle sockets 68, and the dosing carousel is rotated such that a sealed cell containing pharmaceutical is aligned with second passage 30 and third passage 32. Pressure gauge 44 may be inspected to assure that sufficient pressure exists in first passage 28 to operate the inhaler.

Pressing trigger button 66 activates the system, opening metered valve 26 and firing electrostatic charger 40. The open metered valve allows a predetermined amount of gas to expand rapidly into second passage 30, pass through safety valve 46, and impinge on coversheet 20 over entrance 16 of the aligned cell 14 in dosing carousel 12. In order to prevent discharge through an empty cell (and to prevent discharge when the spacer is not fully extended), the system may also include a locking mechanism to prevent accidental discharge.

The expanding gas that impinges on coversheet 20 over entrance 16 explosively ruptures coversheet 20, causing the pharmaceutical to be dispersed and suspended in the gas as it blows in and subsequently impinges on coversheet 22 over exit 18. After pressurizing cell 14 and forming a suspension of the dry powder in the gas, the expanding gas then explosively ruptures exit coversheet 22, further suspending the pharmaceutical in the gas, dispersing any agglomerated particles into powder. In this embodiment, the ports and connectors (if used) form suspension system 38, separately connecting second passage 30 and third passage 32 to the aligned cell 14, and allowing the burst of pressurized gas to separately rupture the coversheets and suspend the pharmaceutical. It is to be understood in this embodiment that the ports may be any structure that adjoins the passages to the openings with a relatively air-tight connection.

Third passage 32 connects the exhaust port to spacer 42, allowing the dry powder suspended in the gas to flow out of cell 14. The dry powder suspended in the gas is directed into and positioned within the spacer for inhalation. The electrostatic charger establishes an electrostatic charge on the chamber. The pharmaceutical, suspended in the gas, is deterred from adhering to the spacer both by the non-stick lining, and the ionizing charge produced by electrostatic charger 40.

After activation of the system, which leads to the introduction of suspension into spacer 42, the patient breathes in the suspension through mouthpiece 24. As the suspended pharmaceutical is inhaled from the spacer, air enters the spacer through air inlet vent 48.

Figure 8:
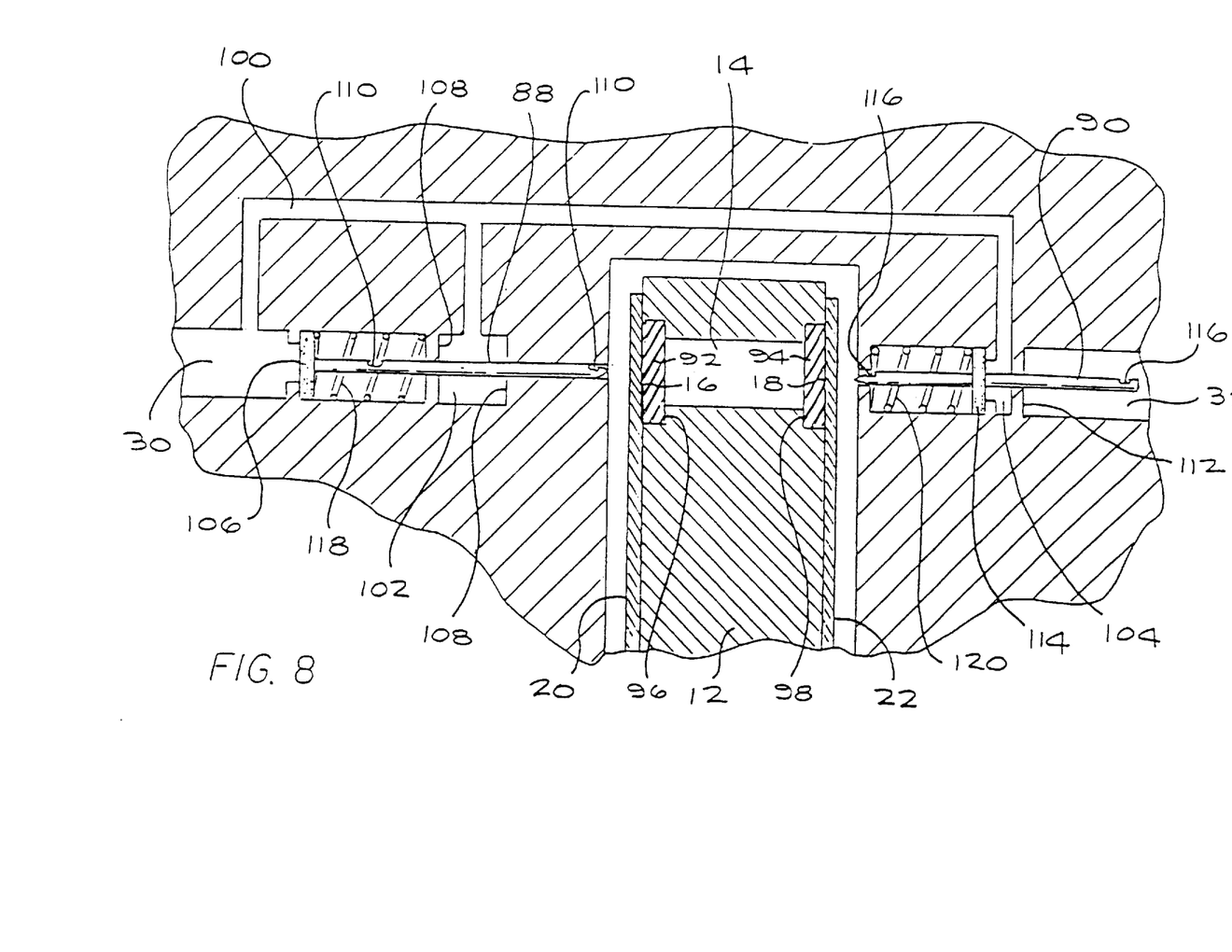
Figure 9:
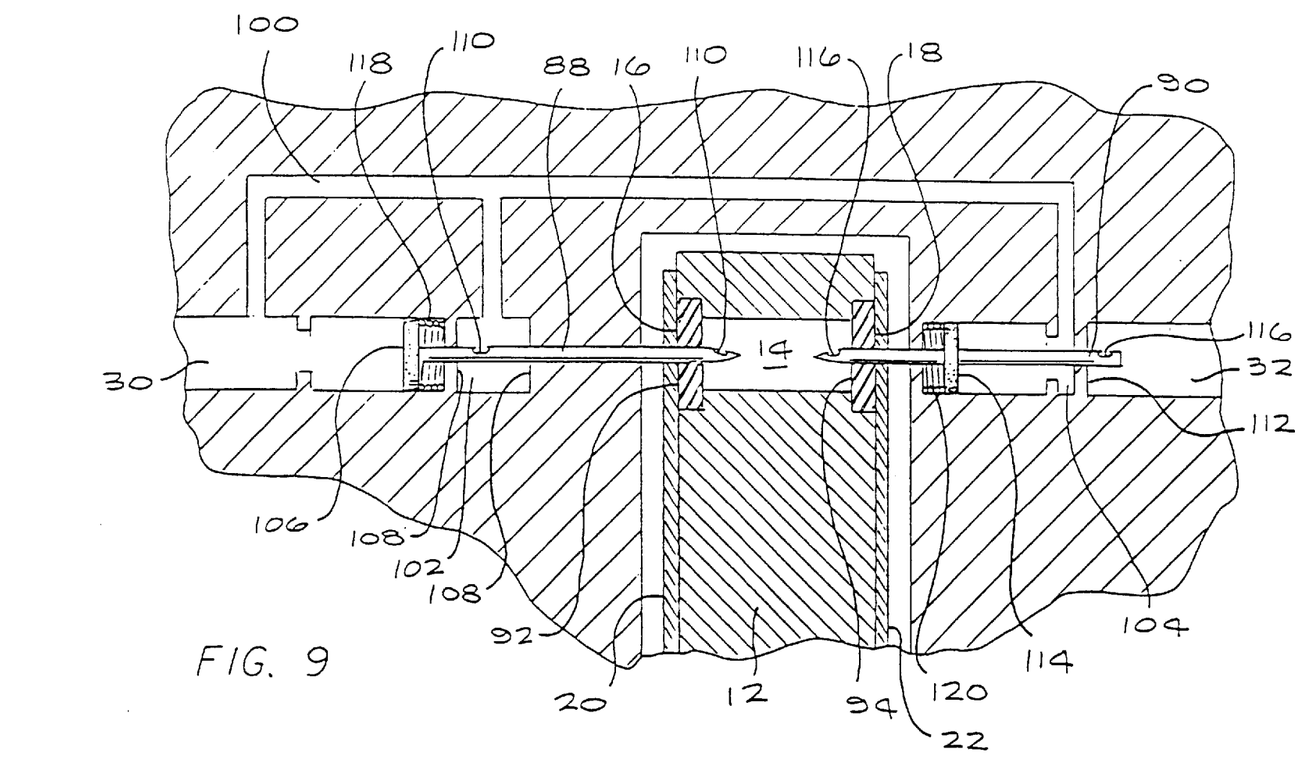

With reference to FIGS. 1, 5, 6 and 8, in another preferred embodiment of the dry powder inhaler according to the present invention (the "dual hollow-needle" embodiment), coversheets 20 and 22 are separately ruptured by entrance and exit hollow piercing needles 88 and 90, forming suspension system 38. Preferably, both entrance 16 and exit 18 include rubber septa 92 and 94 mounted in grooves 96 and 98. The entrance and exit septa are covered by the coversheets, and are likewise pierced by the piercing needles when the coversheets are ruptured. FIG. 9 further depicts the suspension system when rupturing the entrance and exit.

In this embodiment, second passage 30 includes side passage 100 leading to input chamber 102 and piston chamber 104 on opposite sides of dosing carousel 12. Upon activation of trigger 36, the pressurized burst of gas passes down second passage 30 and impinges on a piston 106 attached to entrance needle 88. The entrance needle, which is slidably free and supported by two supports 108, is in turn driven through entrance coversheet 20 and septum 92, rupturing entrance 16.

The burst also travels through side passage 100 to input chamber 102. Hollow entrance needle 88 has holes 110 situated such that when the entrance needle is driven through entrance 16, second passage 30 is connected to the aligned cell 14 through the hollow entrance needle. The burst of gas is then allowed to pass from the input chamber through the entrance needle and into the aligned cell, suspending the dry powder.

Exit needle 90 is slidably free but supported by support 112. At approximately the same time as entrance needle 88 ruptures the entrance 16, the burst travels through side passage 100 to piston chamber 104. The burst of gas enters the piston chamber and impinges on piston 114 that is attached to exit needle 90. The exit needle is in turn driven through exit coversheet 22 and septum 94, rupturing exit 18. The hollow exit needle has holes 116 situated such that when the exit needle is driven through the exit, third passage 32 is connected to aligned cell 14 and the burst of gas is allowed to flow from the aligned cell, through the hollow exit needle and into the third passage. As in the blow-through embodiment, the third passage directs the flow into the spacer, positioning the dry powder and gas in the chamber to dispense the dry powder for inhalation.

After the burst passes out of the aligned cell 14 and the pressure in second passage 30 and side passage 100 returns to normal, springs 118 and 120 (attached to pistons 106 and 114) retract the needles out of coversheets 20 and 22 and septa 92 and 94.

It is noteworthy that the suspension system of this embodiment may not require ports and connectors to create airtight seals with the aligned cell, as were required for the suspension system of the blow-through embodiment. The use of rubber septa 92 and 94 to maintain the air-tight system in dosing carousel 12 may be important in this regard.

In yet another preferred embodiment of the dry powder inhaler according to the present invention, a suspension system similar to the second embodiment may be used, wherein the piercing needles both pierce a single sealed opening to the cell in different locations, separately rupturing that sealed opening to the aligned cell. The needles form separate connections to the cell, and separately connect the cell to the second and third passages. This embodiment does not require a second sealed opening in the aligned cell.

In still another embodiment of the invention, the suspension system may be formed by using a portion of the suspension system described with respect to the blow-through embodiment, and a portion of the suspension system described with respect to the dual hollow-needle embodiment. For example, this embodiment could have a port and connector on the entrance side, and a hollow piercing needle on the exit side.

In yet other embodiments of the dry powder inhaler according to the present invention, a suspension system similar to that described for the blow-through embodiment may further include one or more single spring-loaded piercing needles that separately pierce the coversheets. The needles may aid the impinging gas in separately rupturing the coversheets. The burst of gas would then enter and exit the cell and suspend the pharmaceutical in a fashion similar to that described for the blow-through embodiment. Alternately, there may be one needle that includes two separate hollow segments with holes appropriately placed so as to be equivalent to two separate piercing needles. The burst of gas would then enter and exit the cell and suspend the pharmaceutical in a fashion similar to that described with respect to the dual hollow-needle embodiment. In either of these two embodiments, the needles serve as a suspension system to separately connect to, and rupture, the sealed openings.

By designing the total volume of any of the above described housing systems, including the passages, aligned cell, and input and piston chambers (if applicable), to be small in relation to the volume of gas released by the metered valve into the spacer, the performance of the system is effected only minimally by the gas left in the housing. Preferably, the combined volume of the housing systems is less than 5% of the spacer volume.

A wide variety of pharmaceuticals are contemplated for delivery employing the invention inhalation device and methods described herein. Examples include:

analgesics/antipyretics (e.g., aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate, and the like);

antimigraine agents (e.g., ergotamine tartrate, propanolol hydrochloride, isometheptene mucate, dichloralphenazone, and the like);

sedatives/hypnotics (e.g., barbiturates (e.g., pentobarbital, pentobarbital sodium, secobarbital sodium), benzodiazapines (e.g., flurazepam hydrochloride, triazolam, tomazeparm, midazolam hydrochloride, and the like);

antianginal agents (e.g., beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate, and the like));

antianxiety agents (e.g., lorazepam, buspirone hydrochloride, prazepam, chlordiazepoxide hydrochloride, oxazepam, clorazepate dipotassium, diazepam, hydroxyzine pamoate, hydroxyzine hydrochloride, alprazolam, droperidol, halazepam, chlormezanone, and the like);

antipsychotic agents (e.g., haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like);

antimanic agents (e.g., lithium carbonate), antiarrhythmics (e.g., bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, and the like);

antiarthritic agents (e.g., phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium, and the like);

antigout agents (e.g., colchicine, allopurinol, and the like);

anticoagulants (e.g., heparin, heparin sodium, warfarin sodium, and the like);

thrombolytic agents (e.g., urokinase, streptokinase, altoplase, and the like);

antifibrinolytic agents (e.g., aminocaproic acid);

hemorheologic agents (e.g., pentoxifylline);

antiplatelet agents (e.g., aspirin, empirin, ascriptin, and the like);

anticonvulsants (e.g., valproic acid, divalproate sodium, phenytoin, phenytoin sodium, clonazepam, primidone, phenobarbitol, phenobarbitol sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione, and the like);

antiparkinson agents (e.g., ethosuximide, and the like);

antidepressants (e.g., doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, and the like);

antihistamines/antipruritics (e.g., hydroxyzine hydrochloride, diphenhydramine hydrochloride, chlorpheniramine maleate, brompheniramine maleate, cyproheptadine hydrochloride, terfenadine, clemastine fumarate, triprolidine hydrochloride, carbinoxamine maleate, diphenylpyraline hydrochloride, phenindamine tartrate, azatadine maleate, tripelennamine hydrochloride, dexchlorpheniramine maleate, methdilazine hydrochloride, trimprazine tartrate and the like);

antihypertensive agents (e.g., trimethaphan camsylate, phenoxybenzamine hydrochloride, pargyline hydrochloride, deserpidine, diazoxide, guanethidine monosulfate, minoxidil, rescinnamine, sodium nitroprusside, rauwolfia serpentina, alseroxylon, phentolamine mesylate, reserpine, and the like);

agents useful for calcium regulation (e.g., calcitonin, parathyroid hormone, and the like);

antibacterial agents (e.g., amikacin sulfate, aztreonam, chloramphenicol, chloramphenicol palmitate, chloramphenicol sodium succinate, ciprofloxacin hydrochloride, clindamycin hydrochloride, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, colistin sulfate, and the like);

antifungal agents (e.g., griseofulvin, keloconazole, and the like);

antiviral agents (e.g., interferon gamma, zidovudine, amantadine hydrochloride, ribavirin, acyclovir, and the like);

antimicrobials (e.g., cephalosporins (e.g., cefazolin sodium, cephradine, cefaclor, cephapirin sodium, ceftizoxime sodium, cefoperazone sodium, cefotetan disodium, cefutoxime azotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, and the like), and the like);

anti-infectives (e.g., GM-CSF);

bronchodialators (e.g., sympathomimetics (e.g., epinephrine hydrochloride, metaproterenol sulfate, terbutaline sulfate, isoetharine, isoetharine mesylate, isoetharine hydrochloride, albuterol sulfate, albuterol, bitolterol, mesylate isoproterenol hydrochloride, terbutaline sulfate, epinephrine bitartrate, metaproterenol sulfate, epinephrine, epinephrine bitartrate), anticholinergic agents (e.g., ipratropium bromide), xanthines (e.g., aminophylline, dyphylline, metaproterenol sulfate, aminophylline), mast cell stabilizers (e.g., cromolyn sodium), inhalant corticosteroids (e.g., flurisolidebeclomethasone dipropionate, beclomethasone dipropionate monohydrate), salbutamol, beclomethasone dipropionate (BDP), ipratropium bromide, budesonide, ketotifen, salmeterol, xinafoate, terbutaline sulfate, triamcinolone, theophylline, nedocromil sodium, metaproterenol sulfate, albuterol, flunisolide, and the like);

hormones (e.g., androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), corticosteroids (e.g., triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebulate, prednisolone acetate, prednisolone sodium phosphate, hydrocortisone sodium succinate, and the like), thyroid hormones (e.g., levothyroxine sodium) and the like), and the like;

hypoglycemic agents (e.g., human insulin, purified beef insulin, purified pork insulin, glyburide, chlorpropamide, glipizide, tolbutamide, tolazamide, and the like);

hypolipidemic agents (e.g., clofibrate, dextrothyroxine sodium, probucol, lovastatin, niacin, and the like);

proteins (e.g., DNase, alginase, superoxide dismutase, lipase, and the like);

nucleic acids (e.g., sense or anti-sense nucleic acids encoding any protein suitable for delivery by inhalation, including the proteins described herein, and the like);

agents useful for erythropoiesis stimulation (e.g., erythropoietin);

antiulcer/antireflux agents (e.g., famotidine, cimetidine, ranitidine hydrochloride, and the like);

antinauseants/antiemetics (e.g., meclizine hydrochloride, nabilone, prochlorperazine, dimenhydrinate, promethazine hydrochloride, thiethylperazine, scopolamine, and the like);

and the like.

Additional agents contemplated for delivery employing the invention inhalation device and methods described herein include agents useful for the treatment of diabetes (e.g., activin, glucagon, insulin, somatostatin, proinsulin, amylin, and the like), carcinomas (e.g., taxol, interleukin-1, interleukin-2 (especially useful for treatment of renal carcinoma), and the like, as well as leuprolide acetate, LHRH analogs (such as nafarelin acetate), and the like, which are especially useful for the treatment of prostatic carcinoma), endometriosis (e.g., LHRH analogs), uterine contraction (e.g., oxytocin), diuresis (e.g., vasopressin), cystic fibrosis (e.g., Dnase (i.e., deoxyribonuclease), SLPI, and the like), neutropenia (e.g., GCSF), lung cancer (e.g., beta 1-interferon), respiratory disorders (e.g., superoxide dismutase), RDS (e.g., surfactants, optionally including apoproteins), and the like.

Presently preferred indications which can be treated employing the invention inhalation device and methods described herein include diabetes, carcinomas (e.g., prostatic carcinomas), bone disease (via calcium regulation), cystic fibrosis and breathing disorders (employing bronchodilators), and the like.

While a particular form of the invention has been illustrated and described, it will be apparent that various modifications can be made without departing from the spirit and scope of the invention. Thus, although the invention has been described in detail with reference to preferred embodiments, those having ordinary skill in the art will appreciate that various modifications can be made without departing from the invention.

That which is claimed is:

1. A dry powder inhaler for use with a removable dosing cartridge, wherein said dosing cartridge includes a dry powder in a cell with one or more sealed openings, the dry powder inhaler comprising:

a housing adapted to removably receive a dosing cartridge, the housing defining three passages;

a first valve for controlling the flow of gas from the first passage to the second passage; and a mouthpiece; wherein the first passage includes a connection adapted for connecting to a source of pressurized gas;

the second and third passages have a suspension system for separately connecting to and rupturing the sealed openings of a cell, and additionally for suspending a dry powder; and the third passage is further connected to the mouthpiece.

2. A dry powder inhaler according to claim 1, wherein:

the second passage is adapted to have an entrance port for connecting to one of the sealed openings;

the third passage is adapted to have an exit port for connecting to another of the sealed openings; and wherein said suspension system is comprised of said entrance and exit ports.

3. A dry powder inhaler according to claim 1, wherein said suspension system comprises one or more piercing needles for rupturing the sealed openings.

4. A dry powder inhaler according to claim 1, wherein said suspension system comprises:

a first hollow piercing needle adapted to pierce a sealed opening of the cell and connect the cell to the second passage; and a second hollow piercing needle adapted to pierce a sealed opening of the cell and connect the cell to the third passage.

5. A dry powder inhaler according to claim 1, wherein the source of pressurized gas is a pressurized air cylinder.

6. A dry powder inhaler according to claim 5, wherein the first passage is connected to a pressure gauge.

7. A dry powder inhaler according to claim 6, wherein a passage further contains a safety valve that restricts the flow of gas upon the failure of the first valve to properly restrict the flow of gas.

8. A dry powder inhaler according to claim 1 wherein the inhaler additionally comprises

- a housing with a trigger;
- a hollow spacer connected to said housing, wherein said housing delivers the suspended dry powder into said spacer upon actuation of said trigger;
- a mouthpiece connected to said spacer; and an electrostatic charger adapted to be discharged within said spacer upon actuation of said trigger.

9. A dry powder inhaler according to claim 8, wherein said spacer includes an interior surface coated with a non-stick material.

10. A dry powder inhaler according to claim 9, wherein the non-stick material is Teflon.

11. A dry powder inhaler according to claim 8, wherein said housing is adapted to be retracted substantially into said hollow spacer.

12. A dry powder inhaler according to claim 8, wherein said spacer and said housing may be disconnected and reconnected.

13. A dry powder inhaler according to claim 8, further comprising an air inlet vent adapted to allow inhalation, but not exhalation, through said mouthpiece during operation of the inhaler.

14. A dry powder inhaler according to claim 13, wherein
said housing is adapted to be retracted substantially into said hollow spacer; and
the interior surface of said spacer is coated with Teflon;
said spacer and said housing may be disconnected.

15. A dry powder cartridge inhaler, comprising:
the dry powder inhaler according to claim 1; and
a removable dosing cartridge wherein said dosing cartridge comprises a cartridge body defining at least one cell for containing a pharmaceutical, each of said cells having one or more openings, and further including one or more rupturable coversheets forming an airtight seal over the cell openings.

16. A dry powder cartridge inhaler according to claim 15, wherein:
said cartridge body further defines additional cells for containing a pharmaceutical, each additional cell having one or more openings; and
said coversheets form airtight seals over each of the additional cell openings.

17. A dry powder cartridge inhaler according to claim 16, wherein:
said cartridge body is disk-shaped;
the cells are arranged on said body in a rotationally symmetric pattern around an axis of rotational symmetry; and
each cell has an associated rotation stop included on said cartridge body.

18. A dry powder cartridge inhaler according to claim 15, further comprising:

a trigger connected to said housing;
a hollow spacer connected to said housing, wherein said trigger actuates said first valve causing the suspended dry powder to be delivered into said spacer, and said spacer connects said mouthpiece to the third passage; and
an electrostatic charger adapted to be discharged within said spacer upon actuation of said trigger.

19. A method for using a pressurized gas to dispense a dose of dry powder for inhalation from an airtight cell with one or more sealed openings, said method comprising:
providing an airtight cell with one or more sealed openings having a dose of dry powder therein;
rupturing at least one sealed opening in the airtight cell and blowing a pressurized gas into the cell, thereby pressurizing the cell and forming a suspension of the dry powder in the gas;
separately rupturing one of the sealed openings and allowing the pressurized suspension in the cell to flow out of the cell; and
directing the suspension for inhalation.

20. A method according to claim 19, wherein each rupture is caused by pressurized gas impinging on the sealed openings.

21. A method according to claim 19, wherein one or more piercing needles cause the ruptures.

22. A method according to claim 19, wherein the pressurized gas is provided from a pressurized air cylinder.

23. A method according to claim 19, wherein the airtight cell is formed within a dosing cartridge, the dosing cartridge including a plurality of airtight cells.

24. A method according to claim 19, wherein the flow is directed into a chamber for inhalation, and further comprising the step of establishing an electrostatic charge within the chamber.

25. A method according to claim 24, wherein each rupture is caused by pressurized gas impinging on the sealed openings.

26. A method according to claim 24, wherein one or more piercing needles cause the ruptures.

27. A method according to claim 24, wherein the pressurized gas is provided from a pressurized air cylinder; and the airtight cell is formed within a dosing cartridge, said dosing cartridge further comprising a plurality of airtight cells; said method further comprising venting the chamber to allow in-flowing air during inhalation.

* * * * *